United States Patent
Schwartz et al.

(10) Patent No.: US 6,252,980 B1
(45) Date of Patent: Jun. 26, 2001

(54) ADDITIONAL DYNAMIC FLUID LEVEL AND BUBBLE INSPECTION FOR QUALITY AND PROCESS CONTROL

(76) Inventors: Nira Schwartz; Arie Shahar; Richard Woods, all of 2800 - 187 Plaza Del Amo, Torrance, CA (US) 90503

( * ) Notice: Subject to any disclaimer, the term of this patent is extended or adjusted under 35 U.S.C. 154(b) by 0 days.

This patent is subject to a terminal disclaimer.

(21) Appl. No.: 08/301,812

(22) Filed: Sep. 7, 1994

Related U.S. Application Data

(63) Continuation-in-part of application No. 08/157,734, filed on Nov. 24, 1993, now Pat. No. 5,414,778.

(51) Int. Cl.$^7$ .................................................. G06K 9/00
(52) U.S. Cl. ............................................. 382/141; 356/427
(58) Field of Search ........................... 382/141, 142, 382/192, 194, 270, 271; 348/127, 128; 209/522–528; 250/900, 223 B; 356/240, 427

(56) References Cited

U.S. PATENT DOCUMENTS

| | | | | |
|---|---|---|---|---|
| 3,232,429 | * | 2/1966 | Norwich | 209/524 |
| 4,050,824 | * | 9/1977 | Woodrow et al. | 356/427 |
| 4,172,524 | * | 10/1979 | Holm et al. | 209/524 |
| 4,365,304 | * | 12/1982 | Ruhman et al. | 382/51 |
| 4,429,414 | | 1/1984 | Asakawa | 382/30 |
| 4,606,065 | * | 8/1986 | Beg et al. | 382/18 |
| 4,637,054 | | 1/1987 | Hashim | 382/8 |
| 4,736,851 | * | 4/1988 | Ricros et al. | 209/524 |
| 4,915,237 | * | 4/1990 | Chang et al | 209/524 |
| 5,007,096 | | 4/1991 | Yoshida | 382/8 |
| 5,052,044 | | 9/1991 | Gaborski | 382/32 |
| 5,072,108 | * | 12/1991 | Ishikawa | 356/427 |
| 5,073,708 | * | 12/1991 | Matsumoto et al. | 350/427 |
| 5,136,661 | | 8/1992 | Kobayasi et al. | 382/48 |
| 5,204,911 | | 4/1993 | Schwartz et al. | 382/8 |

* cited by examiner

Primary Examiner—Jon Chang
(74) Attorney, Agent, or Firm—David Pressman

(57) ABSTRACT

Fast image acquisition and image process control are used to advantage to measure dynamic and transient phenomena. This technique distinguishes fluid from bubbles by taking an image of a container containing fluid and modifying the gray levels of the image. Unmodified image processing can be performed without the disadvantage of large time consumption. The technique is used for detecting fluid levels and bubbles, by counting image pixels dedicated to bubbles or to fluid along vertical or horizontal lines within the image. The rate of change of liquid level and the amount of bubbles with time indicate leakage in containers while they are in a dynamic state. The inspection of transient phenomena during a dynamic state gives an indication of the final quality and quantity of a product inside a container. It also provides feedback for the determination of fill nozzle operation, with the advantage of easy calibration and adjustment for the right amount of bubbles within the container. It also provides an indication of mechanical or thermal failures and feedback to indicate any unit which deviates from preset parameters. The system is highly beneficial in the beer and soft drink industry where the taste of the product is highly influenced by the amount of bubbles within the container.

9 Claims, 3 Drawing Sheets

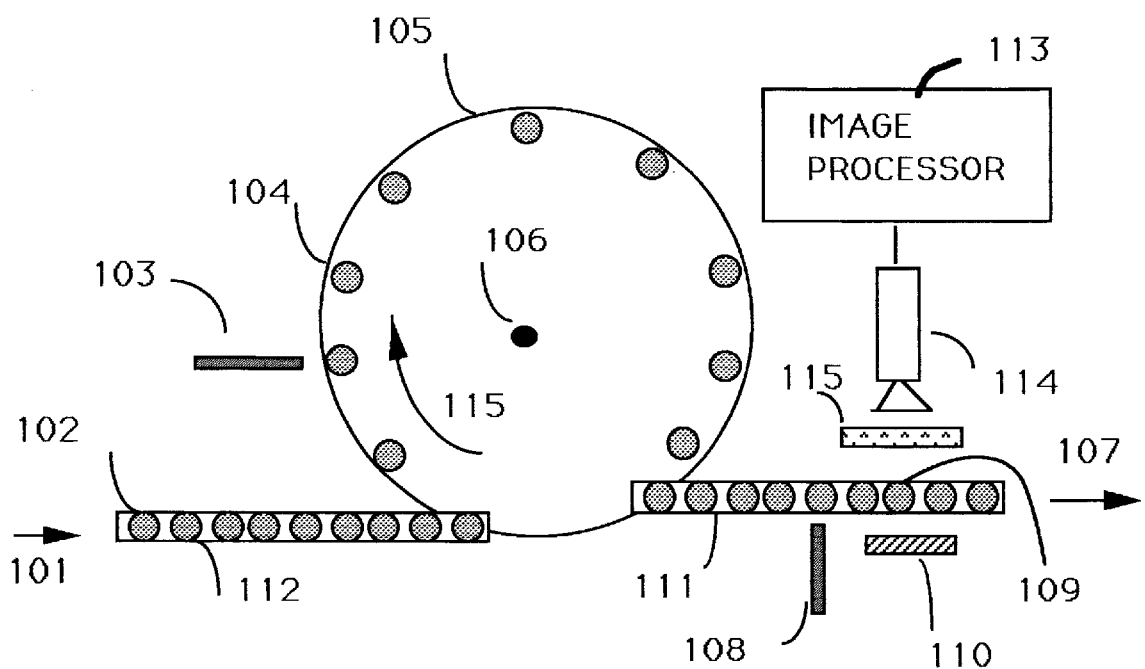
FIG 1 – Prior Art
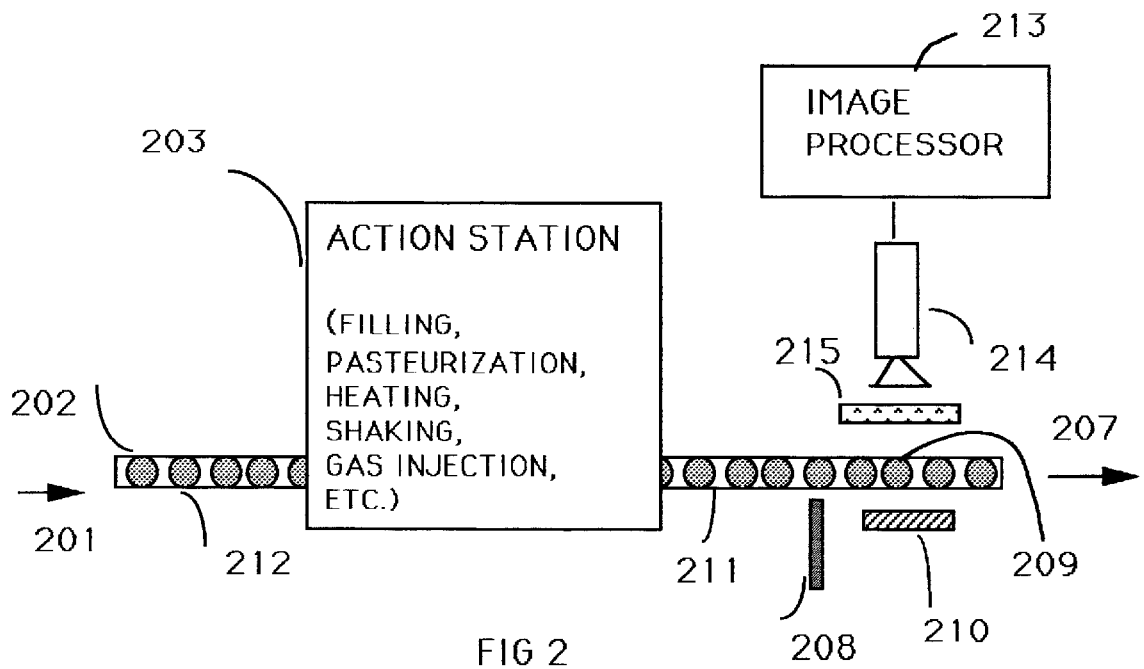
FIG 2

ADDITIONAL DYNAMIC FLUID LEVEL AND BUBBLE INSPECTION FOR QUALITY AND PROCESS CONTROL

CROSS-REFERENCE TO RELATED APPLICATION

This application is a CIP of our co-pending application Ser. No. 08/157,734 filed Nov. 24, 1993 now patent U.S. Pat. No. 5,414,778, granted May 9, 1995.

BACKGROUND

1. Field of the Invention

Generally, the field of this invention relates to quality and process control, particularly to the inspection of dynamic fluid levels in containers as well as suspended bubbles (gas) in the fluid.

2. System of Prior Parent Application

Our above parent co-pending application relates to a system (shown in FIG. 1) for the inspection of containers with a fluid and suspended bubbles in the fluid, where the fluid is in a dynamic state as a result of a filling process at a filling station.

This system is designed to (a) inspect containers while they move on a production line, and (b) predict the container's final fluid level, its pressure, and recommend any needed fill nozzle adjustment. The system contains a light source having a unique wavelength to illuminate the containers being inspected. Images of the inspected containers are modified and stored in a computer's memory for analysis by means of an algorithm. The algorithm is also stored in the computer's memory. However this technique is applicable to an inspection system in the vicinity of the filling station only. It does not apply to inspection at other areas, including areas ahead of the filling station.

OBJECTS AND ADVANTAGES

Accordingly one object of the present invention is to inspect fluid -filled container at areas other than near the filling station, including areas ahead of the filling station.

Other objects are as follows:

(1) to inspect a dynamic fluid for the presence of gas that was intentionally injected into the fluid and to recommend any needed filling adjustment for fluid or gas.

(2) to inspect a dynamic fluid for the presence of unwanted gas that was unintentionally injected into the fluid and to recommend any needed filling adjustment for fluid or gas.

(3) to indicate a malfunctioning filling unit, e.g., one which produces insufficient or no gas and to correlate the malfunctioning unit with inspected containers for quality and process control, (4) to inspect a dynamic fluid that is not supposed to have gas, i.e., to inspect for the presence of unwanted gas in a fluid where the gas was unintentionally injected into the container by a malfunctioning unit.

(5) to indicate a malfunctioning filling unit, e.g., one which creates unwanted gas or air, and to correlate the malfunctioning unit with containers for quality and process control, (6) to indicate a malfunctioning pasteurization unit, e.g., one which creates unwanted gas or air (as a result of over or under heating) and to correlate the malfunctioning unit with an inspected containers for quality and process control, (7) to provide an improved way to predict final fluid level and the amount of dissolved gasses in containers while they move on a production line, (8) to indicate the quality of the fluid within the container and whether the container's cap is properly sealed, (9) to predict a liquid's viscosity as a function of the rate bubbles in the liquid are dissolving,

(10) to create a dynamic state of fluid and bubbles by the use of thermal or mechanical forces to implement inspection past the filling or the pasteurizing station,

(11) to provide improved an way to inspect a pasteurization process by the amount of gas or air for quality and process control,

(12) to inspect ungased dynamic fluids for the existence of bubbles for quality and process control, and

(13) to correlate a fill nozzle on a filling carousel with an inspected container for easy nozzle adjustment for the right amount of fluid and bubbles inside a container, thereby to provide an automatic alarm if one of the nozzles on the carousel is off calibration.

Further objects and advantages will become apparent from a consideration of the ensuing description and accompanying drawings.

BRIEF DESCRIPTION OF DRAWINGS

FIG. 1 is a schematic view of a prior-art fluid filling system employing an image processor for quality and process control.

FIG. 2 is a schematic view of a system with an action or force creating station for producing a fluid in a dynamic state, employing an image processor in accordance with the invention.

GENERAL SUMMARY OF THE METHOD

Figure 3:
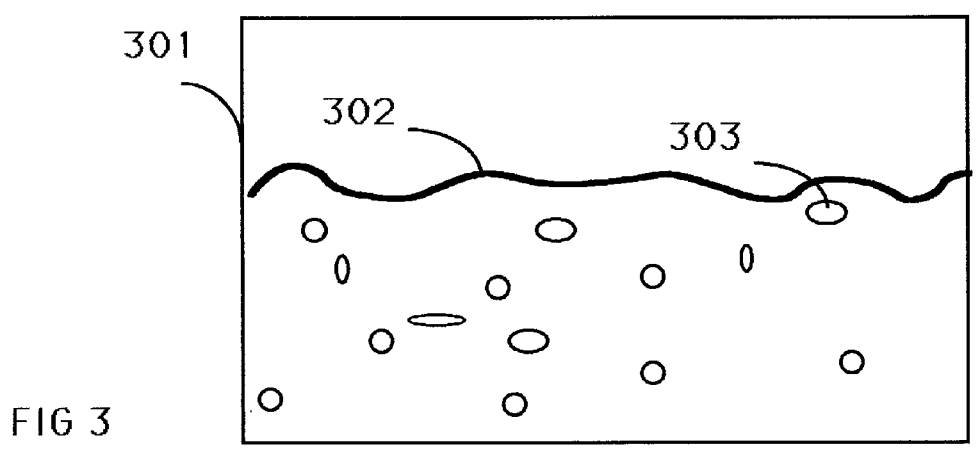
FIG. 3 is a view of a cameras field of view showing a fluid level and bubbles within the fluid in accordance with the invention.

The method of the invention comprises the following sequential steps:

(1) An action unit operates with mechanical or thermal forces on containers filled with fluid that are moving on a production line.

(2) The fluid level inside a container is scanned optically while the fluid is in a dynamic state. The dynamic state is created by a mechanical force, a thermal force, or both. The scan produces a product image having gray levels (3) Gray levels of neighbor pixels of the product image are compared to distinguish bubbles from liquid, or the gray levels in the image are modified or quantized.

(4) The fluid height is measured once or several times. Inspection results are saved and plotted as the graph of FIG. 7.

(5) The amount of bubbles (gas) within the fluid is measured once or several times.

(6) The data from the measured fluid height (step 3) and bubble measurement (step 4) are correlated to the action unit using a mathematical function (7) The fluid height, the amount of bubbles and the rate of change of fluid height and bubbles are analyzed and compared with the dynamic range and behavior of an acceptable product.

(8) The container is tested for leaks by analyzing the dynamic behavior of the fluid and the bubbles.

(9) The container is tested for quality and process control.

Each of the above steps will now be considered separately in detail.

FIG. 1—Filling Carousel-Prior Art

The prior-art inspection system of our parent application is able to inspect containers filled with dynamic fluid and bubbles as shown in FIG. 1. This system comprises a measuring system employing a sensor 108 located a short distance after a filling carousel 105. This system inspects the dynamic processes within each container. This location is used because the fluid inside containers 109 is still active due to the filling operation so the bubbles can be easily seen. This location is also especially good for glass containers because they cannot be squeezed to simulate a dynamic condition.

Incoming containers 102 move in a direction 101 on an input conveyor 112 to be picked up by a carousel 105. Nozzles 104 on the carousel are used for filling the containers with fluid and dissolved gases. The carousel rotates about axis 106 in a clockwise direction 115. The containers leave the carousel on an output conveyor 111. Bottle sensors 103 and 108 are used to correlate a particular container on output conveyor 111 with a specific fill nozzle. Camera 114 and image processor 113 take images of the containers as they move along conveyor 111.

After filling at carousel 105, the fluid inside container 209 is in a very active transient condition or dynamic state. This dynamic state is easy to detect electronically. This eliminates the need to shake the container to cause the gas to separate from the fluid.

A plurality of images of container 109 are taken or acquired by camera 114 and processor 113. Image processor 113 counts pixels in the container's image. This system also inspects the amount of bubbles inside the containers, the rate at which they dissolve, and the viscosity of the liquid. The containers may include water, beer, wine, liquid medicine, oil, blood, or any other fluid.

The images are stored in the memory (not shown) of processor 113. Camera 114 has a field of view which includes the surface of the container's liquid level as well as the bubbles in the liquid. This field of view is shown in FIG. 3, The gray levels of the image are modified (quantized) in a known manner to distinguish liquid from bubbles. This is done by selecting a threshold level for liquid and for bubbles and applying a lookup table of the vision system (explained below) as described, e.g., in U.S. Pat. No. 5,204,911, granted to Schwartz et al., Apr. 20, 1993.

Figure 4:
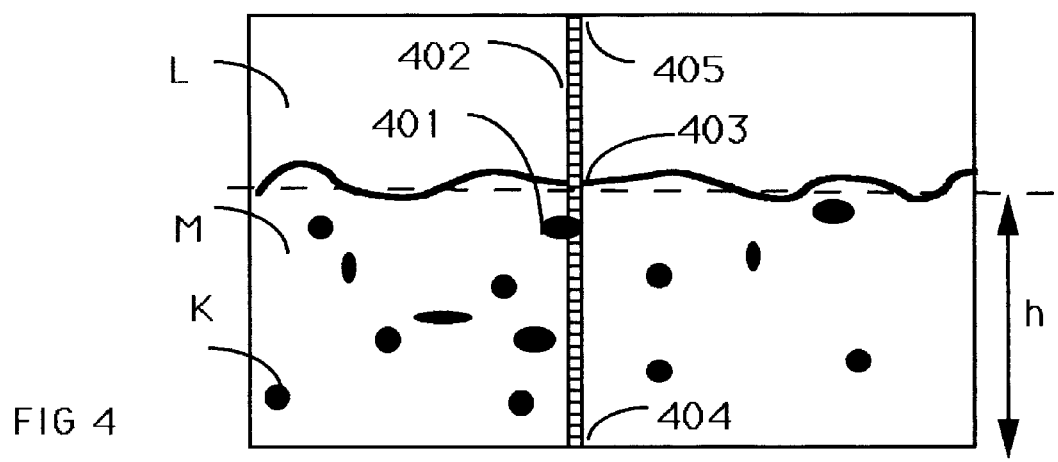
FIG. 4 is a measurement of the fluid's height along one column within the camera's field of view, in accordance with the invention.

The liquid height is measured by counting the number of pixels relating to the fluid along each line (or column) of the modified image, as will be explained in conjunction with FIG. 4 below. In FIG. 4 the fluid image is modified to have gray levels of value M. Counting of pixels can be performed by the vision system. This is done by using the vision system's histogram feature, i.e., by defining a 'window' or area of interest (AOI) inside an image as one line only. The resultant scan will be a histogram vector which is a count of the number of pixels with equal gray level values. Therefore it is a count of pixels with gray levels of value M, the value to which the fluid image's gray levels were modified. In the present case it is the number of pixels of fluid along the vertical line.

Figure 5:
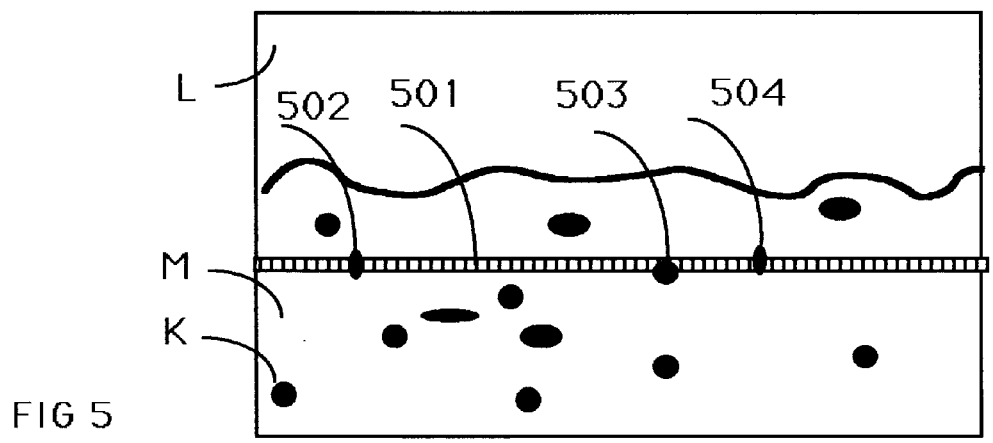
FIG. 5 is a the measurement of the bubbles along one row within the camera's field of view, in accordance with the invention.

Another fast way to count pixels while using a vision system is described in the above U.S. Pat. No. 5,204,911. In the system of this patent, the template image is an assembly of lines of different gray levels. The template is superposed with a modified image as shown in FIGS. 4 or 5. The histogram of the superposed images will resolve with the counts of pixels along vertical or horizontal lines. Averaging the count values will indicate the average liquid level. This system preferably employs a Model 150/151 image processor made by Imaging Technology Inc. of Woburn, Mass.

The bubbles are measured by counting the number of pixels of the bubbles along each line (or column) of the modified image. The count value indicates the amount of bubbles inside the liquid. Since a plurality of images are acquired, a plot of liquid heights, or amount of bubbles as a function of time is generated. The rate of change of each plot, and a comparison with a good containers behavior, predict the viscosity of the liquid, as well as the existence of any leaks in the container.

Processor 113 counts the number of bubbles, the height of the fluid during a period of time, and then compares the dynamics of each container to determine if the fluid inside behaves within predefined deviations. The results are then compared to a good container's behavior, which has been previously stored in the processor, and are also compared to the operation of other nozzles on the carousel. The sensors enable the quick identification of faulty nozzles which may require adjustment.

Modifying Product Image

The gray level values of the product image are modified in order to quantize such levels to distinguish bubbles from liquid. This is done in real time using lookup tables and existing hardware, as fully shown in FIG. 2 below.

The system of FIG. 1 is known in the art

FIG. 2—Present System—Action Station

A main difference between prior-art inspection systems, including the system of FIG. 1, and the present inspection system relates to the types of forces which create a dynamic state in the fluid and the bubbles. These forces are different and are classified as mechanical, thermal, or both. Also the present inspection system looks for the existence of wanted or unwanted gas/air bubbles in the fluid for quality and process control.

FIG. 2 show containers 202 that move on input conveyor 212 in direction 201, towards an action station 203. The action station operates on the containers. The action station can be a filling station, a heating (pasteurization) station, a gas or air injection station, a shaking station, and any combination of the above. After treatment at the action station, the containers move in direction 207 on output conveyor 211. The containers are sensed with a known sensor 208 to correlate inspected containers, such as 209, with action units, such as nozzles or heating pads (not shown), inside the action station. Such correlation is performed within processor 213 in a known manner. Inspection is performed by the use of a light source 210 and/or 215, camera 214, and image processor 213.

The current inspection process looks not only for bubbles in the fluid that are expected to be there, but also for bubbles that are not expected to be there. For example if the action station fills the containers with fluid only (no gas) and inspection of the containers shows bubbles of gas or air in some or all of the containers, this indicates a malfunction. Also an excessive amount of bubbles may be an indication of a failure of a nozzle on filling carousel, or another problem that the maintenance engineers must correct.

A case where an excessive amount of bubbles is not tolerated occurs during and after a pasteurization process. This may indicate overheating the container, causing the product to disintegrate. Correlating the container that was overheated with the heating unit is very important for in process and quality control. Elimination of the source that creates an excessive amount of bubbles prolongs the shelf life of the product dramatically, e.g., two times longer.

So, while the system of FIG. 2 uses an image processor 213 identical to that of prior-art processor 113 of FIG. 1, it measures different physical phenomena. In both cases the system counts pixels. However the FIG. 2 system counts, in the container's image, pixels which display different physical phenomena, originated by different forces. Indeed to an outside observer it may look like the same physical phenomena, since bubbles are the same wherever found. However different mathematical equations will be needed to describe the present case. They may involve different parameters, such as defects size on the fill nozzle, amount of heat injected into an inspected container, fluid temperature, and much more. Different mathematical equations are needed to describe different physical phenomena. The mathematical equations are very complicated and most of the time impossible to solve. This present system tries to overcome this mathematical difficulty by inspecting the fluid's behavior, analyzing its images, predicting quality, and establishing correlation of the action station and an inspected container for process control.

The present system also inspects the amount of bubbles inside the containers, the rate at which they dissolve, and as a result the viscosity of the liquid. The containers may include water, beer, wine, liquid medicine, oil, blood, or any other fluid. The present inspection system uses those counts in a unique manner to predict final static value of liquid level, amount of dissolved gas, and to evaluate liquid viscosity.

After action station 203, the fluid inside the container is in a very active transient condition. This dynamic state is easy to detect by the presence of suspended bubbles in motion, by the change of fluid height with time, by the dissolving of bubbles (gas/air) in the fluid, and by the presence of fluid motion inside the container.

A measuring system employing a sensor 208 is located a short distance after filling action station 203. This system inspects the dynamic processes within each container. This location is used because the fluid inside containers 209 is still active and the bubbles can be easily seen.

A plurality of images of container 209 are acquired by camera 214 and processor 213, and are stored in the memory (not shown) of processor 213. Camera 214 has a field of view which includes the surface of the container's liquid level as well as the bubbles. This field of view is shown in FIG. 3.

The gray levels of the image are modified (as in prior art system) to quantize them so as to distinguish liquid from bubbles. This is done by selecting a threshold level for liquid and for bubbles and applying a lookup table of the vision system.

However, in the case of containers which move at slow speed (slow throughput), it is not necessary to quantize (modify) the image gray levels to distinguish fluid from bubbles. Adjusting the output video signal from camera 214 to the input of image processor 214 to brighten the image will do the job as well. In this case the image includes a multiplicity of gray level values. Counting pixels can be done by the use of methods well known in the art, such as edge detection, blob detection, filtering, and other methods. Those methods are considered slow, i.e., they require a lot of time and therefore have a disadvantage with respect to the method where the image gray levels are modified to distinguish bubbles from liquid. For example the image gray levels can be modified to have only two gray levels, and, a histogram vector can be made only two places long (for the two gray levels) rather than 128 places long (for the standard gray level camera). A vector two places long can be processed much faster than a vector 128 places long. Both of the methods will resolve with the same data.

The liquid height is measured by counting the number of pixels relating to fluid along each line (or column) of the modified image, as will be explained in conjunction with FIG. 4 below. In FIG. 4 the fluid image is modified to have gray levels of value M. Counting of pixels can be performed by the vision system. This is done by using the vision system s histogram feature, i.e., by defining a window or area of interest (AOI) inside an image as one line only. The resultant scan will be a histogram vector which is a count of the number of pixels with equal gray level values. Therefore it is a count of pixels with gray levels of value M, the value to which the fluid image's gray levels were modified. In the present case it is the number of pixels of fluid along the vertical line. Another fast way to count pixels while using a vision system like Image Technology, Inc.'s Model 150/151 processor, is described in above U.S. Pat. No. 5,204,911, where the template image is an assembly of lines of different gray levels. The template is superposed with a modified image as shown in FIGS. 4 or 5. The histogram of the superposed images will resolve with the counts of pixels along vertical or horizontal lines. Averaging the count values will indicate the average liquid level.

The bubbles are measured by counting the number of pixels of the bubbles along each line (or column) of the modified image, as be explained in conjunction with FIG. 5 below. Counting of pixels is performed by setting the vision system to define a 'window' or area of interest (AOI) inside an image as one line only. The resultant histogram count will be a vector which is a count of the number of pixels With equal gray level values. Therefore it is a count of pixels with gray levels of value K, the value to which the bubble image's gray levels were modified. In the current case it is the number of pixels of bubbles along the vertical or horizontal line. Another fast way to count pixels while using a vision system is defined in above U.S. Pat. No. 5,204,911, where the template image is an assembly of lines of different gray levels. Averaging the count values will indicate the average liquid level.

Figure 6:
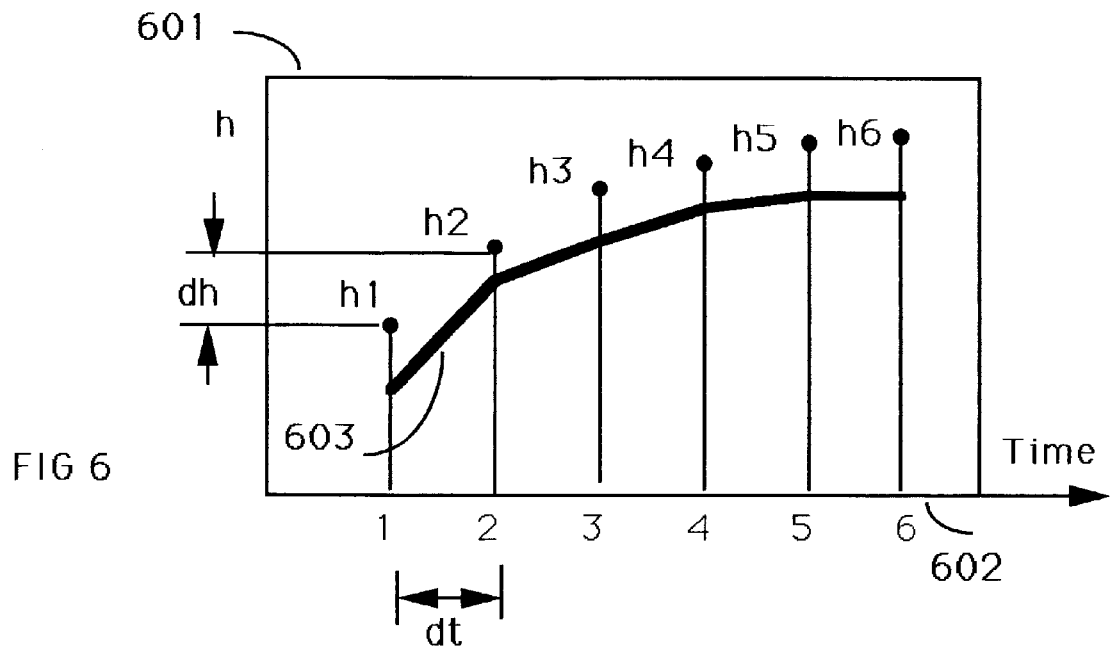
FIG. 6 shows the fluid level height asymptotically approaching a static value, in accordance with the invention.
Figure 7:
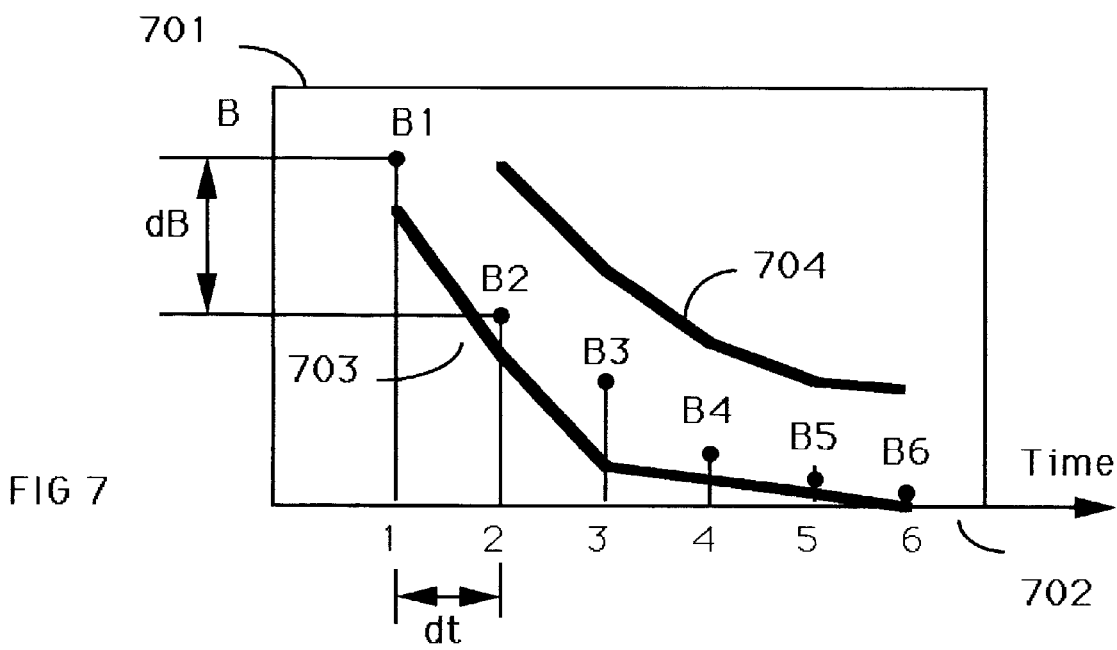
FIG. 7 shows the amount of bubbles asymptotically approaching a static value as they dissolve within the fluid, in accordance with the invention.

The count value indicates the amount of bubbles inside the liquid. Since a plurality of images are acquired, a plot of liquid heights, or amount of bubbles as a function of time, is generated (FIGS. 6 and 7). The rate of change of each plot, and a comparison with a good container's behavior, predict the viscosity of the liquid, as well as the existence of any leaks in the container.

Processor 213 counts the number of bubbles and the height of the fluid during a period of time, and then compares the dynamics of each container to determine if the fluid inside behaves within predefined deviations. The results are then compared to a good containers behavior, which has been previously stored in the processor, and are also compared to the operation of other nozzles on the carousel. The sensors enable the quick identification of faulty nozzles which may require adjustment.

Modifying Product Image

Modification of the gray level values of the pixels of the product image, using lookup tables, is done in real time using existing hardware. The gray levels are modified or quantized in order to distinguish pixels representing bubbles (gas) from pixels representing liquid and to make it easier and therefore faster on the counting process. (Other methods can distinguish bubbles from liquid). The tables are loaded with data during startup of the computer. The data define the conversion function change ir real time. For reference see the operating manual, "Lookup Tables" (LUT), Technical Publications Department, 1990, Image Technology, Inc., Woburn, Mass. The lookup tables are used to modify the gray levels of the image.

The lookup tables are loaded with a transform function. The transform function is unique for each product and is well known to those skilled in the art. E.g., the transformation function for a beer bottle is as follows: all gray levels in the product image between 0 to 150 (i.e., below threshold level 150) are converted to gray value 0, and all gray levels between 151 and 255 converted to gray level 160.

The image acquired by camera 214 and shown in FIG. 3 is modified to have bubbles displayed as dark gray levels, as shown in FIGS. 4 and 5. This is done according to the lookup tables. This makes it possible to count pixels related the two groups, pixels related to liquid and pixels related to bubbles. The vision system is able to count liquid height by counting the number of pixels related to the fluid inside the container. Each image is composed of plurality of pixels aligned in columns and rows. The counts takes place along a line which is a column or row in the modified image. The final fluid height is obtained by averaging the counts over the number of lines that pixels were counted, as explained in detail in equations (1) and (2) below.

This modification of the image gray levels is performed with the aid of back light source 215 in FIG. 2. Light rays from source 215 shine toward mirror 210, are reflected from the mirror, pass through the fluid inside the container, and then travel back to camera 214. That makes it possible to have the camera and the light source on the same side of the conveyor, providing mechanical and optical advantages. The camera should be slightly above the light source so that light coming from the container will be collected. A simpler configuration where the camera is on one side of the conveyor and the light source is on the other side of the conveyor is also possible.

However, in case the containers have slow throughput speed, it is not necessary to modify the image gray levels to distinguish fluid from bubbles. Adjusting the output video signal from camera 214 to the input of image processor 214 to brighten the image will do the job as well. In this case the image includes a multiplicity of gray level values. Counting pixels can be done by the use of methods well known in the art, such as access by the processor to each of the image's pixels by address or by intensity (gray level), edge detection, blob detection, filtering and other methods. As stated, methods are considered slow, i.e., they require a long processing time and are not as good as modifying the image gray levels.

However, when the containers have a slow throughput speed, it is not necessary to modify the image to distinguish fluid from bubbles and gain fast counting process. However since the image contains a plurality of gray levels, the time consumption of counting pixels with gray levels which relate to bubbles or fluid is significantly larger, as we will show below.

FIG. 3—Dynamic State Inside Container

In order to follow the dynamic behavior of a fluid, multiple images of the container are required. Today's computer technology is fast enough to acquire multiple images, and the method described in our above application parent application is fast enough to perform the image processing in real time.

FIG. 3 illustrates a single image 301, which is field of view 107 of container 102 (FIG. 1), or the neck of container 209 (FIG. 2). Multiple images of container 209 are acquired by camera 214 and are stored in the memory of processor 213 (FIG. 2). Images are acquired at equally spaced times.

The container's fluid level 302 is a wavy line, indicating that the fluid is in a dynamic state. The existence of bubbles 303 also indicates that the fluid is in a dynamic state. The image gray levels (not shown) contain many gray levels, some representing fluid and others representing bubbles. These gray levels are modified so that the fluid is expressed as one gray level (M, FIG. 4) and the bubbles as another gray level (K, FIG. 4).] This is done by selecting a suitable gray level threshold. The selected gray level threshold is the one allowing the maximum number of pixels related to bubbles to be shown in the modified image. If the threshold is not selected correctly, fewer bubbles are shown in the image. In the example previously given, under "Modifying Product Image", the gray level range was 0 to 255, so that the threshold level must be within this range.

First the threshold is selected as value 0. Then it is increased to be of value 1, and so on. For each threshold selection, the number of pixels related to bubbles are counted. The threshold with the maximum bubble pixels is selected. All the gray levels above that threshold are converted to one gray level value. All gray levels below that threshold are converted to another gray level value, thereby to form an image with two gray level values.

A ternary image with three gray level values can also be provided, as shown in FIG. 4. One gray level value K is for bubbles, a second gray level M is for the fluid, and a third gray level L is for the medium (air) above the fluid's surface. A ternary image is used whenever the camera's field of view includes three types of media.

A camera's field of view may includes multiple types media. E.g., another situation when more than two gray level values is used occurs if container includes several types of fluids, layered on top of each other. That case will require a specific gray level value for each layer of fluid inside the container. A suitable threshold level is unique to each product and is selected experimentally.

FIG. 4—Measuring Fluid Height in Dynamic State

FIG. 4 is similar to FIG. 3, and is used to demonstrate the procedure of measuring the fluid level height inside a container while the fluid is in a dynamic state.

The gray levels (not shown) of FIG. 3 are modified by the use of the LUTs of processor 213. They appear as shown in FIG. 4, where bubbles such as 401 are darkened and set to a gray level K, versus the bubbles in FIG. 3 which have multiple gray levels. Using the same procedure for gray level modification, the gray levels of the fluid (below wavy line 302 in FIG. 3) are modified to be of value M, different that of the air domain (above line 302 in FIG. 3) which is modified to be of a gray level value L. The gray level of the bubbles is different from that of the liquid and from the air domain above the liquid's wavy surface.

A long vertical line or column 402 is used to calculate fluid height 403. The vision system is selected to scan one vertical line as an area of interest (AOI)). The histogram feature is constrained to count pixels within the selected AOI only. The processor is set to move the AOI from line to line so that the entire body of fluid will be covered in real time and in sequential order. Different AOIs are possible on the same image. Vertical line 402 is a modified image line composed of a row of pixels. E.g., distance between point 403 and point 404 is 25 pixels. This will be the height of the fluid along line 402 in a static state, i.e., a fluid without bubbles.

As stated, the fluid is in a dynamic state, and there is a bubble 401 with two pixels long along vertical line 402. The actual height of the fluid will be less than 25 pixels by the height of bubble 401, i.e., 23 pixels. The processor will count only pixels with gray levels of value M (23 of them) between a bottom point 404 of the image and point 403. Since bubble 401 is two pixels long, i.e., two pixels with gray value K, those pixels are not counted. Therefore the actual height of the fluid along vertical line 402 will be two pixels short of point 403 and equal to 23 pixels.

The procedure will be repeated for all possible vertical lines parallel to line 402 inside the image. An RS170 standard camera can take 512 vertical lines parallel to line 402. The fluid height related to the first vertical line is A1, to the second vertical line is A2, and so on. Each of the counts A1, A2, and so on, is stored in the memory of processor 213. All of the counts are summed by the processor logic unit and divided by the number of counts. The total fluid height is the average height of all of these vertical counts measurements and is expressed as the value h.

$$h=(1/N) \times [A1+A2+ \ldots +A402+A512] \quad (1)$$

where N equals the total number of vertical lines. The value of h is shown in FIG. 4 as the distance in pixels and it expressed the average height of the fluid in a dynamic state.

The h value of the fluid inside the container as a function of time (at successive positions along the production line) is plotted in FIG. 6. Note that the h value rises asymptotically, indicating that the gas in the container is dissolving and the fluid is reaching its static state.

It is also possible to count pixels with gray levels without modifying the gray levels of the acquired image, as explained below.

The basic approach is the direct access method, where the image processor has access to the gray level value of each of the pixels in the image. Access can be obtained by address or by intensity. Each pixel has an address which identifies its position within the image. Each pixel has an intensity expressed by a gray level value. Access can be obtained, for example, to all the pixels in the image with a given gray level to acquire their address or to a specific address to acquire that pixel's gray level value. The processor can acquire their intensity values and store them in a memory. Then a threshold pixel gray level is defined so that any pixel with a gray level value above the threshold is counted as a fluid pixel and a gray level below the threshold is counted as a bubble pixel. Then two processor counters are assigned) one for the bubbles and one for the fluid. Each time the processor detects a fluid pixel, it also raises the fluid count by one. Each time the processor detects a bubble pixel, it raises the bubble count by one. The processor sequentially accesses all the image pixels or just an area of interest (AOI). A line or column within the image is identified as an AOI.

The procedure of accessing each pixel and the comparison of its gray level with the threshold level is done by software which requires a large amount of processing time. This is because the software algorithm is slow compared to hardware functions. Modifying the image gray level and using the hardware histogram function for counting pixels with gray levels is much faster than the software way and therefore preferable.

Pixels are counted a long vertical line 402 to calculate fluid height 403. The vision system is selected to scan one vertical line as an area of interest (AOI). The processor is set to move the AOI from line to line to cover the entire body of fluid in real time and in sequential order.

Vertical line 402 is an image line composed of a row of pixels. The image processor compares intensity values of pixels along line 402 in sequential order. Pixels next to each other are compared for intensity values for boundary detection. (The image processor has access to each of the pixels by position and value). For example, a boundary pixel (related to a bubble boundary or a fluid boundary) can be selected easily. Whenever the change of pixel gray level value on top and below a selected pixel (along line 403) is more than 10% of the average gray level, the selected pixel is declared a boundary pixel.

The average gray level can be defined as the summation of ten gray level values of ten neighbor pixels divided by ten. Several methods of edge detection are well known in the art, and may also be used to detect the edge (surface) of a bubble. Progressing along the line 403 and counting pixels between boundaries indicates the fluid height and bubbles sized in number of pixels.

For example, the distance between point 403 and point 405 is 40 pixels. Three boundaries are detected: the first 20 pixels away from point 404, the second 22 pixels away from point 404, and the third at 27 pixels away from point 404. The conclusion is that the bubble size is two pixels long and the fluid level height along line 402 is 25 pixels, excluding the bubble height. This is only one way of counting pixels and measuring dimensions. This method is considered slow and should be applied only in the case of containers which move at a slow throughput speed.

The fluid height will be again evaluated by the same averaging procedure that took place in the prior art and, as explained above, after the image is modified.

FIG. 5—Measuring Bubbles in Dynamic State

FIG. 5 is also similar to FIG. 3, and it demonstrates the procedure of measuring the number of bubbles expressed by the number of pixels within a container with the fluid in a dynamic state.

The gray levels of FIG. 3 are modified by the use of the LUTs of processor 213. They appear as shown in FIG. 5, where the bubbles are darkened and set to a specific gray level K, versus the ones in FIG. 3 which have multiple gray levels (not shown). The gray level of the bubbles is different from that of the liquid and from the air domain above the liquid's wavy surface. Using the same procedure for gray level modification, the gray levels of the fluid are modified to be of value M, different that of the air domain, which has a gray level value L.

A long horizontal line 501 is used to calculate the number of bubbles The vision system is selected to have one horizontal line as an area of interest (AOI). The processor's histogram feature is set to count pixels within the selected AOI only. The AOI can be moved from line to line to cover the entire body of fluid in real time and in sequential order. Horizontal line 501 is a modified image line composed of a row of pixels. The number of bubbles are expressed as a number of pixels. Bubbles 502 503, and 504 lie along horizontal line 501, and have gray levels of value K, which is different from the gray level M of the fluid. The height of bubble 502 along horizontal line 501 is two pixels, the height of bubble 503 is three pixels, and the height of bubble 504 is two pixels. Processor 106 (FIG. 1), or processor 213 (FIG. 2) is set to count only pixels with gray level value K. Therefore it will count the number of pixels representing bubbles along horizontal line 501. The count value will be 2+3+2=7 pixels.

The procedure will be repeated for all horizontal lines parallel to line 501 in the liquid. An RS170 standard camera can take 480 horizontal lines parallel to line 501. To save processing time, the procedure is repeated only over a preselected number of lines. The number of lines depends upon the type of gas dissolved, the temperature of the liquid, and the pressure inside the container. For a standard beer bottle, the number of lines selected was 20. The total number of pixels representing the amount of bubbles along horizontal line 501 is B501 (B501 equals the number of pixels representing bubble 502, plus those representing bubble 503, plus those representing bubble 504, i.e., five pixels as calculated in the previous paragraph). The amount of bubbles will be decrease with time as the fluid approaches a stable state where the gas is completely dissolved.

The total number of pixels representing the bubbles in the first horizontal line is B1, in the second horizontal line is B2, and so on. Each of the counts B1, B2, and so on, is stored in the memory of the processor 213. All of the counts are summed by the processor logic unit and divided by the number of counts. The total amount of bubbles can be expressed as the average of all of these horizontal count measurements and is expressed as the value B.

$$B=(1/N)\times[B1+B2+ \ldots +B480] \quad (2)$$

N equals the total number of horizontal lines on which counts where performed. (N=480 if camera RS170 is used and if bubbles are counted along all of the horizontal lines).

The total number of pixels representing the bubbles along one row may also be repeatedly counted over a period of time and averaged.

The number of pixels representing bubbles along horizontal line 501 are saved in memory for further analysis.

The value B for the average amount of bubbles as a function of time is plotted in FIG. 7.

It is still possible to count pixels with gray levels without modifying the gray levels of the acquired image as explained in the last section under the discussion of FIG. 4, The same counting procedure is applied to horizontal image lines, instead of vertical image lines.

FIG. 6—Plot of Fluid Level in Dynamic State

FIG. 6 is a time plot of the value h, the fluid level of FIG. 4. This was measured six times at equally spaced intervals, as represented by the dots at the tops of the ordinates. The behavior of h is exponential. At the value h=h6, the height of the fluid has reached its static value. The value of h6 can be obtained by extrapolation with time within a small error using the first three values, h1, h2, and h3. The rate of change of value h with time (dh/dt) is a good indicator of the viscosity of the fluid and its ability to hold dissolved gases. I.e., the greater dh/dt, the greater the fluid's viscosity (Measuring beer bottles in one embodiment gave dh/dt values of 500, 200, 70, and 10 pixels per 0.5 sec).

Plot 603 is statistically obtained by inspecting good bottles, i.e., found to be within fluid final acceptance levels. Inspection results are saved and plotted as the graph of FIG. 7. As long as newly inspected bottles have a fluid height behavior above plot 603, the line operator will be assured that the static fluid level height will be within the acceptable range. A higher statistical range (not shown) represents overfilling.

Nozzle 204 on the carousel is adjusted according to the result of FIG. 6. For example, if static height h6 is lower than line 603, then the opening of nozzle 204 should be increased to allow more fluid to pass into the container.

FIG. 7—Plot of Bubbles Dissolved in a Dynamic State

FIG. 7 is a time plot of the value B from FIG. 5. The value of B was measured six times at equally spaced intervals. The behavior of B exponentially decays. At the value B=B6 the gas in the fluid has reached its static value. The time that it will take the bubbles to dissolve (B6) can be obtained by extrapolation within a small error using the first three values, B1, B2, and B3. The rate of change of value B with time (dB/dt) is a good indicator of the viscosity of the fluid and its ability to hold dissolved gases. I.e., the greater dB/dt, the greater the viscosity of the fluid.

If dB/dt is small, this indicates that there are not enough bubbles in the container. This can be as a result of a leak where bubbles escaped the containers, or it can indicate that not enough gas was injected into the container. Both cases require a rejection of the product. If that situation occurs for the same nozzle, it indicates that the nozzle must be adjusted to inject more gas. It may also indicate a mechanical problem with the nozzle. In both cases the process quality engineer must be alerted.

Plots 703 and 704 are statistically obtained by inspecting good bottles, i.e., those found to be with final acceptance levels for dissolved gases and acceptable product taste (as defined by the manufacturer). Inspection results are saved and plotted as the graph of FIG. 7. As long as the bubble behavior of newly inspected botdes is between plots 703 and 704, their dissolved gases and tastes will be within the acceptance range.

SUMMARY, RAMIFICATIONS, AND SCOPE

Accordingly, the reader will see that we have provided a method that will enable the inspection of fluid bubbles within a container, as well as the fluid fill level, while both are in a dynamic state. This provides control of the quality of the product. It also provides a method for predicting seal cap leakage by analyzing the exponential decaying of the bubbles to a steady state and estimating and controlling the final fluid level in the container by analyzing the behavior of the fluid's height. We also provide a method for predicting the final static liquid level inside the container by analyzing the behavior of the fluid's height during the dynamic mode. Further, we can correlate the individual bottles with the filling carousel's nozzle to enable specific nozzle adjustment without affecting the whole filling machine. We also provide a way to calibrate the amount of gas that a nozzle injects into the container by inspecting the rate of change of bubbles inside the liquid in a dynamic state. Also by analyzing asymptotic behavior of liquid height and amount of bubbles, we provide viscosity values of liquids. We also provide a way to predict mechanical failures that introduced any undesired gas (air, carbon dioxide etc.) in the fluid. We also provide a way to monitor pasteurization and heat control. This is done by inspecting fluid and bubble behavior after the pasteurization station, comparing it with a standard container's behavior, and correlating this to the action station upon failure to match a pre-established quality level. This is done for process control to determine any malfunction in the action station.

While the above description contains many specific details, these should not construed as limitations on the scope of the invention, but as exemplification of the presently preferred embodiments thereof. Many other ramifications and variations are possible within the teachings to the invention.

For example, other forces can create the dynamic force, such as nuclear radiation, X rays, and sonic waves.

In another example, we can shake the container to create a dynamic fluid condition inside the container. However this creates a need for extra hardware.

Therefore, the scope of the invention should be determined, not only by examples given, but by the appended claims and their legal equivalents.

What is claimed is:

1. A method for monitoring an action station on a production line where containers which contain liquid pass through said action station and experience a force which causes said liquid to be in a dynamic state, comprising:

(a) causing a plurality of containers which contain liquid to pass through said action station sequentially, (b) operating on each container at said action station so that said liquid in each container is in a dynamic state when each container leaves said action station and so that said dynamic state asymptotically approaches a final level after each container leaves said action station, (c) inspecting optically at several successive times the liquid level in each of said containers to obtain several liquid levels for each of said containers as said dynamic state asymptotically approaches said final level and saving said liquid levels for each of said containers as a plurality of saved liquid levels, and (d) analyzing said saved liquid levels in order to monitor said action station and predict a future final liquid level.

2. The method of claim 1, further including calibrating said action station for prediction of said container's future fluid level based upon said saved liquid levels.

3. A system for monitoring an action station on a production line where containers which contain liquid pass through said action station and experience a force which causes said liquid to be in a dynamic state, comprising:

(a) an action station means, (b) transport means for causing a plurality of containers which contain liquid to pass through said action station means sequentially, (c) said action station means arranged to operate on each container at said action station means so that said liquid in each container is in a dynamic state when each container leaves said action station means and so that said dynamic state asymptotically approaches a final level after each container leaves said action station means, (d) inspecting station means for optically inspecting at several successive times the liquid level for each of said containers for obtaining several liquid levels as said dynamic state asymptotically approaches said final level and saving said liquid levels for each of said containers as a plurality of saved liquid levels, (e) analyzing means for analyzing said plurality of saved liquid levels in order to monitor said action station and predict a future final liquid level.

4. The system of claim 3 wherein said action station means is calibrated for future prediction of each container's final fluid level based upon said plurality of saved liquid levels.

5. A method for monitoring an action station on a production line where containers which contain liquid pass through said action station and experience a force which causes said liquid to be in a dynamic state, comprising:

(a) causing a plurality of containers which contain liquid to pass through said action station sequentially, (b) operating on each of said containers at said action station so that said liquid in each container contains a plurality of bubbles when each container leaves said action station and so that said bubbles asymptotically are absorbed to a final absorption level after each container leaves said action station, (c) inspecting optically at several successive times the bubble level in for each of said containers to obtain several bubble levels as said bubbles asymptotically approach said final level and saving said bubble levels as a plurality of saved bubble levels, and (d) analyzing said plurality of saved bubble levels in order to monitor said action station and predict a future final liquid level.

6. The method of claim 5, further including calibrating said action station for prediction of said container's future fluid level based upon said plurality of saved bubble levels.

7. A system for monitoring an action station on a production line where containers which contain liquid pass through said action station and experience a force which causes said liquid to be in a dynamic state, comprising:

(a) an action station means, (b) transport means for causing a plurality of containers which contain liquid to pass through said action station means sequentially, (c) said action station means arranged to operating on each container at said action station means so that each of said containers contains liquid and possible bubbles in a dynamic state when each container leaves said action station means, where the level of said liquid asymptotically approaches a final level, (d) inspecting station means for optically inspecting at several successive times the liquid level for each of said containers for obtaining several liquid levels as said dynamic state asymptotically approaches said final level and saving said liquid levels as a plurality of saved liquid levels for each of said containers, (e) analyzing means for analyzing said plurality of saved liquid levels to provide an analysis, and (f) correlating said analysis with said action station for process control.

8. The system of claim 7 wherein said inspection station means is arranged to inspect said liquid to obtain said liquid levels.

9. The system of claim 7 wherein said inspection station means is arranged to inspect said bubbles to obtain said liquid levels.

* * * * *